United States Patent [19]

Hsiung et al.

[11] Patent Number: 4,614,200

[45] Date of Patent: Sep. 30, 1986

[54] HAIR TREATING METHOD AND COMPOSITION

[75] Inventors: Du Y. Hsiung, Park Forest; Billye J. Branch, Country Club Hills; Jayaseelan Rathnam, Des Plaines, all of Ill.

[73] Assignee: Helene Curtis Industries, Inc., Chicago, Ill.

[21] Appl. No.: 509,648

[22] Filed: Jun. 30, 1983

[51] Int. Cl.$^4$ ............................................. A45D 7/00
[52] U.S. Cl. .......................................... 132/7; 424/70
[58] Field of Search ................. 132/7, 9, 79 R, 79 A, 132/DIG. 3; 424/70, 71, 68

[56] References Cited

U.S. PATENT DOCUMENTS

| | | | |
|---|---|---|---|
| 2,707,697 | 5/1955 | Wainer | 132/7 |
| 3,208,910 | 9/1965 | Cassidy | 132/7 |
| 3,266,994 | 8/1966 | Reiss et al. | 424/71 |
| 3,840,401 | 10/1974 | Umezawa et al. | 8/127.51 |
| 3,842,847 | 10/1974 | Hewitt et al. | 132/7 |
| 4,151,272 | 4/1979 | Geary et al. | 424/68 |
| 4,206,195 | 6/1980 | Bolich, Jr. et al. | 132/9 |
| 4,206,196 | 6/1980 | Davis | 132/9 |

FOREIGN PATENT DOCUMENTS 0888689 12/1971 Canada.

*Primary Examiner*—John J. Wilson
*Attorney, Agent, or Firm*—Dressler, Goldsmith, Shore, Sutker & Milnamow Ltd.

[57] ABSTRACT

A method of treating hair to strengthen and improve its physical properties and a composition useful therein is disclosed. More particularly, the composition contains polyvalent metal salts and the hair, so treated, is substantially hydrophobic and bodied.

2 Claims, No Drawings

HAIR TREATING METHOD AND COMPOSITION

TECHNICAL FIELD

This invention relates to a method of treating hair to strengthen and improve its physical properties and to a composition containing polyvalent metal salt for use thereon. More particularly, the hair treating method and composition provides substantial hydrophobicity and long-lasting body to the treated hair.

BACKGROUND ART

Normal hair is sometimes naturally so fine and limp and so lacking in body that it does not hold a hair set well. Frequently, the hair becomes even less bodied and is sometimes weakened as a result of being subjected to multiple chemically active cosmetic treatments, such as permanent waves and tints. Additionally, hair may be further weakened and weathered by other contributing factors, such as bleaching by exposure to sun and chlorinated swimming pool water.

Normal hair is also usually hydrophobic. However, many of the previously mentioned chemical treatments remove the natural hydrophobic components from the hair. Consequently, the relative porosity of the hair increases as its hydrophobicity decreases. As the porosity of the hair increases, it tends to pick up water and swell more readily. When the hair is weakened and porous, it is more vulnerable to stretching and breaking while it is water-swollen.

Routine grooming inevitably requires that wet hair be mechanically stretched and manipulated during shampooing, combing and setting on curlers. Additionally, currently popular hairstyles are achieved by "blow-drying" the freshly washed hair. In the "blow-dry" procedure, the hair is not set on curlers; rather the wet hair is brushed continuously until it is dry while a stream of heated air from a hand-held electric hair dryer is directed over the portion of the hair being brushed. Thus water-swollen hair that is in a weakened physical condition may snap and break or be mechanically damaged during blow drying.

This invention relates to a method of treating hair to strengthen it and improve its physical properties by treating the hair with compositions containing a water-dispersible non-toxic polyvalent metal salt of a mineral acid. The hair is strengthened by restoring its hydrophobicity and decreasing its porosity. The physical properties of the hair are improved by long-lasting conditioning benefits that resist removal by water or subsequent shampoo washings. The polyvalent metal salts have a cation selected from the group consisting of aluminum (III), cerium (III) and (IV), iron (III) and zirconium (IV) and an anion of a strong mineral acid.

Polyvalent metal salts are generally appreciated in the art primarily for their astringent effects on skin for antiperspirant activity. Hewitt et al. in U.S. Pat. No. 3,842,847, taught the use of astringent water-soluble salts of aluminum, hafnium, zirconium and zinc and the like in a shampoo and hair treatment to diminish scalp perspiration. By diminishing the perspiration on the scalp, less sebum transferred to the hair, so the hair stayed cleaner longer. Hewitt et al. reported antistatic, as well as anti-soiling, effects with aqueous rinses of aluminum chlorohydrate present in concentrations of at least 0.004 weight percent, preferably from 2 to 6 weight percent. The researchers believed the aluminum salt reacted with the hair keratin making it less anionic in nature and thus less "fly-away." However, for the purposes intended by Hewitt et al., the pH of the treatment and shampoo compositions were limited to the operable astringency range of the metal salts from 3 to 6.5. Also the hair had to be water rinsed after treatment until the pH of the rinse water was at least over 6.

The effectiveness of the method of this invention, as explained below, is not dependent on the astringent action, if any, of the polyvalent metal salt of aluminum or zirconium selected for use in hair-treating compositions used herein. For example, zinc salt, one of the astringent materials taught by Hewitt et al. is ineffective to achieve the results of this invention. Further the hair treating compositions of this invention, including those containing aluminum and zirconium salts similar to those taught by Hewitt et al., need not be rinsed from the hair. Indeed, the compositions are preferably allowed to remain in contact with the hair as explained below, and are effective for the purpose intended at salt concentrations well below known levels recognized for astringent antiperspirant effects.

Cassidy in U.S. Pat. No. 3,208,910, taught the use of a water-soluble zirconium carboxylate salt in a hair styling fluid for imparting body, moisture resistance and sheen to human hair. Zirconium acetate present in a concentration of 0.1 to 2 percent at a pH from about 3 to 6 was used for setting the hair. However, the hair tended to behave as if it were full of snarls and was extremely difficult to comb if the concentration exceeded 2 percent. Consequently, body and moisture-resistant effects could only be increased by including auxiliary dispersing agents, waxes and polymers or by washing the hair with a soap shampoo and forming an insoluble zirconium soap on the hair. The compositions of this invention are not so restricted, and the zirconium salts practiced as taught herein are those which were rejected by Cassidy as being less effective than carboxylate salts.

Commercially available products usually rely on resins or polymeric materials to produce bodying effects on the hair. However, these products usually provide no hydrophobic improvement against the known adverse effects of humidity in maintaining a hair style. In some cases, these materials make the hair hard to comb or may, themselves, absorb moisture. Attempts have been made to make hair hydrophobic by means of products that are applied to the hair in the form of oily hair dressings and creams where the product is left on the hair to act as a physical barrier against moisture. However such products provide a temporary effect that is removed when the user washes her or his hair. Frequently these products weigh the hair down with a dull coating, thereby sacrificing the bodying benefits desired by persons having fine, limp, porous hair. Thus, consumers face a dilemma in choosing which physical characteristics they wish to improve and which desirable characteristics they are willing to sacrifice to get the desired improvement.

A desirable hair treatment product, therefore, would strengthen the hair, especially porous hair, and provide a cosmetically pleasing, lasting improvement in the physical properties of hair.

BRIEF SUMMARY OF THE INVENTION

A method of treating hair for purposes of strengthening and improving the physical properties thereof is disclosed comprising the steps of contacting the hair with an aqueous hair treating composition including about 0.001 to 10 weight percent of a water-dispersible, non-toxic polyvalent metal salt having a cation selected from the group consisting of aluminum (III), cerium (III), cerium (IV), iron (III), zirconium (IV), aluminum zirconium coordination complexes and mixtures thereof. More particularly, the treatment restores hydrophobicity to hair and provides body. The effects last through subsequent washings with shampoo and are not removed by water.

As practiced under the method of this invention, a composition useful therein can be easily applied to wet or dry hair by means of a rinse or leave-on method of application. Particularly beneficial effects are seen when weakened porous hair is so treated. Weakened porous hair is denoted herein as hair that has been subjected to one or more tintings and/or permanent waving treatments, especially of the chemically reactive type.

Porous hair that is treated by the method taught herein with the compositions of this invention is strengthened by being made more hydrophobic and less porous in comparison to the hair before the treatment. Additionally, improvements in the physical properties of the treated hair are beneficially demonstrated by a fluffier, more bodied appearance of the hair, improved manageability and in improved maintenance and retention of hair sets.

Another advantage of the method disclosed is that the hair treating composition accomplishes its effect when used either as a simple solution of salt in water and, preferably, when the salt is included in a cosmetic emulsion form. Conventional conditioner materials may be included to augment the treatment and do not interfere with its effectiveness.

It is particularly to be noted that the benefits of strengthening the hair as described in the method of this invention will be appreciated during blow-drying procedures. Hair treated as practiced herein is more hydrophobic so it is less swollen when it is water wet. Thus it is stronger and more able to withstand the stretching and pulling action of the brushing on the wet hair fibers. Thus as practiced in the method herein, a hair-treating composition is further useful as a strengthening styling agent for grooming the hair.

Still further benefits and advantages of the present invention will become apparent to those skilled in the art from the detailed description of the invention, the examples and the claims which follow.

DISCLOSURE OF THE INVENTION

A method of treating hair is described capable of strengthening and improving the physical properties thereof comprising the steps of contacting the hair with an aqueous composition including about 0.001 to about 10 weight percent of a water-dispersible, non-toxic polyvalent metal salt having a cation selected from the group consisting of aluminum (III), cerium (III), cerium (IV), iron (III), zirconium (IV), aluminum zirconium coordination complexes and mixtures thereof. A hair treating composition useful herein can include cationic, nonionic and anionic and amphoteric emulsifiers, conditioners (including cationic conditioners), oils, and emollients selected from among known materials used for their conventionally employed cosmetic purposes in the art. Alternatively, the hair treatment is effectively practiced even if the hair-treating composition is in the form of an aqueous solution of the selected salt. The pH value of the composition can be within the range of about 2 to about 7, preferably from about 3 to about 5.

Polyvalent metal salts found particularly useful in improving the physical properties of hair in the method described below include the following inorganic salts of strong mineral acids: The inorganic salt that consists essentially of complex basic aluminum chloride loosely associated with about 2.5 moles of water commonly known as aluminum chlorohydrate; aluminum chloride hexahydrate; aluminum sulfate octadecahydrate; cerium (III) nitrate hexahydrate; cerium (IV) acid sulfate; iron (III) chloride hexahydrate; iron (III) sulfate hydrated with about 5 to 6 moles of water; iron (III) nitrate nonahydrate; zirconium oxychloride octahydrate; aluminum zirconium coordination complexes and mixtures thereof.

A particularly preferred polyvalent metal coordination complex may be aluminum chlorohydrate complexed with propylene glycol or polyethylene glycol in which some of the water molecules normally coordinated to the aluminum ion in aluminum chlorohydrate have been displaced by the glycol resulting in a relatively less polar complex of lower water content. This complex is defined and identified as aluminum chlorohydrex in the *CTFA Cosmetic Ingredient Dictionary*, 3rd Edition, published by the Cosmetic Toiletry and Fragrance Association, Inc. Also preferred is aluminum zirconium tetrachlorohydrate complexed with glycine in which some of the water molecules normally coordinated to the metal have been displaced by the glycine; and a loosely hydrated polymeric complex of aluminum zirconium chloride. Exemplary coordination complexes are commercially available from the Reheis Chemical Company, sold under the trademark Rehydrol II, Rezal 36G, Rezal 36GP, Rezal 67GP. Hereinafter, the coordination complexes will be referred to by their common name, or commercial trademark.

In the method of this invention a hair treating composition can be applied as a rinse to the hair as described in the examples below. In a rinse method, the composition may be applied to wet or dry hair maintained in contact with the hair for a period of time from about five seconds to about sixty minutes. The excess composition may be removed from the hair by rinsing the hair further with water or by subsequently washing the hair with shampoo in the usual manner. Preferably, the compositions may be applied directly to wet or dry hair in a leave-on procedure also described below. In a leave-on procedure, the composition is allowed to dry on the hair and maintained thereon without rinsing for a period of at least 6 to about 24 hours.

What is surprising is that the physical properties of the hair, especially porous hair, treated in the foregoing manner are improved in hydrophobicity and body, as disclosed below. It is to be understood that the expression "improvement in the physical properties of the hair" refers to an increase in the hydrophobicity of the hair, an increase in the body of the hair, a decrease in the porosity of the hair, an increase in maintenance of a hair set hereafter referred to as "set retention," an improvement in the visual appearance and behavior of dry hair exemplified by a soft, fluffy appearance as opposed to a clumped look. This improvement lasts through subsequent washings with commercial shampoo products.

The mechanism of the reaction is not fully understood. It is believed, however, that the metal cation is absorbed onto and into the hair to form ionic complexes with the negative sites in the hair or to form coordination bonds with amino nitrogen, oxygen or sulfur atoms in the hair. These metal complexes formed are stable and are not removed by subsequently rinsing the hair with water or by subsequently washing the hair with conventional non-soap detergent shampoo products.

The concentration of the previously described salt can vary from about 0.001 to about 10 weight percent, preferably from about 0.01 to about 1 weight percent. Concentrations in excess of about 10 weight percent may be used, but do not contribute to the effectiveness of the compositions. It is to be understood that the term "salt" refers hereinafter to polyvalent metal salts having a cation of aluminum, cerium, iron, zirconium and aluminum zirconium coordination complexes as previously described.

The effectiveness of this hair treatment method in strengthening and improving the physical properties of hair is particularly enhanced on porous hair, defined above. The relative porosity of the hair can be determined by measuring the amount of liquid the hair retains when it is immersed in water. A well known method of measuring liquid retention values is described in Example 7. Liquid retention values for hair that has been tinted and for hair that has been bleached and subsequently waved, referred hereinafter as bleached/waved, are in the range of about 40 to about 60 weight percent respectively. Consequently, when the hair is in such a porous condition, it has a greater tendency to weaken and break when it is wet. In the hair treating method of this invention, a hair treating composition strengthens porous hair by increasing the hydrophobicity of the hair, thereby lowering the liquid retention value of the treated hair.

As practiced herein, the treated hair, especially previously porous hair, assumes a desirable soft fluffy appearance on drying. Hair fluffiness is believed to be related to the hydrophobicity of the hair surface; i.e., the spreading of water over the hair surface. Porous hair fibers, when they are wet, tend to be sticky and usually adhere to one another. Consequently, the hair dries in clumped, stiff strands that make the hair hard to comb and give it an unattractive appearance. By increasing the hydrophobicity of the porous hair as practiced herein, it is believed that the ability of the hair fibers to adhere to each other lessens. Thus, the treated hair dries to a substantially normal fluffy state and has a surprising amount of body. It is to be understood that the term "body" is usually interpreted by the consumer as that quality which gives her hair greater fullness, greater volume and firm, bouncy curls, and that allows the consumer to achieve and maintain a desired hair style or hair set.

Tinted and bleached/waved hair usually has little or no body. However, substantially good to excellent body is achieved when this type of hair is treated under the method herein as described in the example below. Set maintenance is usually evaluated by well-known set retention methods which measure changes in the length of the initial curl when it is subjected to a highly humid atmospheric ambient condition. It is well known that temporary curls can be achieved by setting the hair with water and drying it on conventional curlers. It is also well known that such curls are easily relaxed under high humidity so that the temporary set is lost. Porous hair is particularly susceptible to losing its set for the aforementioned reasons. The hair treatments practiced herein improve set retention as illustrated in the examples below under ambient room conditions having a relative humidity of about 50 to about 60 percent.

Particularly surprising are the findings that the hair treatments practiced herein strengthen and improve the physical properties of the hair, especially porous hair, at operable salt concentrations of as low as 0.01 weight percent. Further surprising is that hair so treated can be bodied without coating or stiffening the hair with undesirable dulling material even when the composition is allowed to dry on the hair.

Additionally, the treatments were effective even when relatively high concentrations of cationic conditioners were present which normally make the hair soft and limp.

For purposes of demonstrating the effectiveness of the hair treatments practiced herein, most of the hair treating compositions used in the examples below are simple aqueous solutions of a polyvalent metal salt.

Other ingredients may also be included in the composition selected from among known fragrances, coloring agents, preservatives, thickeners, and auxiliary hair setting resin materials. The compositions may be used in the form of a water thin liquid, whether emulsified or not, liquid spray, gel, and cream.

This invention is further illustrated in the following examples, which are not intended to be limited.

BEST MODE FOR CARRYING OUT THE INVENTION

In the examples which follow, references will be made to certain procedures and test materials. For convenience, these are described immediately hereafter.

I. Float/Sink Test Of Hydrophobicity

This test procedure evaluates the hydrophobicity of hair after treatment with the compositions disclosed below:

Dry hair fibers were cut to about 0.635 cm (about ¼ inch) in length and weighed to about 0.02 gram. The hair fibers were spread out on a piece of glazed paper within a one square centimeter area. The fiber mass was transferred from the paper and placed gently on the surface of water ( about 40 ml of water in a 50 ml beaker). The length of time the fiber mass remained floating before sinking into the water was recorded.

If the hair was hydrophobic, it would float on the surface for over an hour. Hydrophilic hair fibers, on the other hand, would sink into the water within 30 seconds. Under this test, normal untreated virgin hair was hydrophobic whereas hair that had been chemically treated with an oxidative hair tint, bleach and/or permanent wave products was hydrophilic.

II. Water-droplet Spreading Test Of Hydrophobicity

This test procedure evaluates the hydrophobicity of hair after treatment with the compositions disclosed below.

A tress of dry hair about 6 inches in length (about 15.24 centimeters) and 2 grams in weight was placed on a flat surface, combed and smoothed to align the fibers. The tress was anchored at both ends with adhesive tape to keep the fibers aligned. A drop of water was placed onto the surface of the hair using a conventional dropping pipette and its spreadability timed.

Under this test, the water-droplet would spread over the hair surface immediately if the hair was hydrophilic, for example: tinted or bleached and waved. If the hair was hydrophobic, as for example normal untreated virgin hair, the water droplet would spread over the hair only after a much longer period of time elapses.

III. Preparation Of Test Samples Of Tinted Hair

Test samples of oxidatively dyed hair were prepared as described below for use in evaluating the compositions disclosed below. Hereinafter, any reference to tinted hair refer to tresses receiving the following multiple dye treatments.

Naturally dark brown tresses of normal human hair (DeMeo Brothers, New York) about 6-inches in length and 2 grams in weight were dyed for 25 minutes at room temperature, using a commercial oxidative-type hair dye of a light hair shade following the product directions. The dyed tresses were washed with a commercial shampoo in the usual manner at the end of the coloring procedure. The tresses were redyed as above two more times for a total of 3 dye treatments. The resulting hair color was light brown.

The liquid retention value of tinted hair prepared in this manner was about 40% thereby simulating values normally observed in on-head situations.

IV. Preparation Of Test Samples Of Bleached/Waved Hair

Test samples of bleached and waved (bleached/waved) hair were prepared as described as follows for use in evaluating the compositions disclosed below. Hereinafter, any references to bleached/waved hair refers to hair tresses so treated.

Naturally dark brown tresses of normal human hair (DeMeo Brothers, New York) about 6-inches in length and 2 grams in weight were bleached in a first step by immersing the tresses in an aqueous solution containing 3 weight percent hydrogen peroxide adjusted to a pH value of about 10.3 with ammonium hydroxide. The temperature of the bleaching solution was maintained at about 32 degrees C. during a bleaching treatment period of 30 minutes. The bleached tresses were rinsed with water and then washed in the usual manner with a conventional commercial non-soap, detergent shampoo.

In a second step, the above bleached tresses were subsequently given a permanent wave while they were in a straight configuration. The freshly shampooed tresses from step 1 were lightly towel blotted and combed to detangle the fibers. The tresses were then immersed in a commercial thioglycolate-containing permanent wave lotion diluted to a strength of 0.2N SH with distilled water. The pH value of the diluted lotion was 9.3. The hair tresses were treated over a 30-minute treatment period to form partially reduced hair and were then water rinsed for about 2 minutes. The partially reduced hair tresses were then neutralized by immersing them in an aqueous solution containing 6 weight percent hydrogen peroxide having a pH value of about 4 for about 5 minutes. The neutralized tresses were water rinsed and washed in the usual manner with a conventional non-soap, detergent shampoo.

The liquid retention value of bleached/waved hair prepared in this manner was about 60%, thereby simulating values observed in on-head situations.

V. Rinse And Leave-On Methods Of Treating Hair

The hair treatment methods practiced herein included a "Leave-on" procedure and a "Rinse" procedure. Briefly described, in a leave-on procedure the composition can be applied by pouring it or spraying it onto dry or wet hair. The composition can be rubbed or combed into the hair and is dried and left on for at least 6 to about 24 hours without any intervening water rinse or shampoo. In a rinse procedure, the composition can be similarly applied and allowed to remain on the hair for a period of about 5 seconds to about 60 minutes.

For convenience, the details of the steps used for purposes of illustrating the effectiveness of the hair treatment methods in the following examples will be referred to hereinafter by the identifying procedural code below.

| Rinse Method | Step | PROCEDURE |
|---|---|---|
| A | (1) | The composition was applied to a dry hair tress, and rubbed through the hair to coat the hair fibers. |
|  | (2) | After a one-minute treating period, the tress was rinsed with water, combed and dried under ambient room conditions. |
| B | (1) | The tress was washed with a commercial nonsoap, detergent shampoo in the usual manner and blotted with a towel. |
|  | (2) | The procedure of Method A was then followed. |
| C | (1) | The complete procedure of Method A was followed. |
|  | (2) | After the hair had dried, the tress was washed with commercial shampoo as in step 1 of Method B. |
| D | (1) | The complete procedure of method B was followed. |
|  | (2) | After the hair had dried, the tress was washed with shampoo as in step 1 of Method B. |
| E | (1) | The composition was applied to a dry hair tress anb rubbed through the hair to coat all the fibers. |
|  | (2) | The treated tress is combed to neatly align the fibers. |
| F | (1) | The tress was washed with a commercial shampoo following step 1 of Method B. |
|  | (2) | The procedure of Method E was followed. |
| G | (1) | The complete procedure of Method E was followed. |
|  | (2) | After 24 hours the dry tress was washed following the procedure of step 1 of Method B. |
| H | (1) | The complete procedure of Method F was followed. |
|  | (2) | After 24 hours the dry tress was washed with shampoo as in step 1 of Method B. |

It is to be understood that method G and H are classified as Leave-on procedures because the purpose of the shampoo step is merely to demonstrate the stability and substantivity of the treatment to removal by washing. Thus, the Leave-on method simulates a hair groom or hair setting product use. A period of 24 hours was selected because it is well known that many consumers wash their hair daily.

The amount, of composition applied to the hair was 1 to 1½ grams per gram of hair in all tests.

VI. Glossary Of Polyvalent Salts Tested

In the examples which follow certain polyvalent salt compounds will be referred to, so for convenience, references to the compounds will be made only by their common name or commercial trademark.

(a) Aluminum sulfate is $Al_2(SO_4)_3 \cdot 18H_2O$ (b) Aluminum chloride is $AlCl_3 \cdot 6H_2O$ (c) Chlorohydrol is a 50% solution of aluminum chlorohydrate sold under this tradename by Reheis Chemical Company.

(d) Rehydrol II is a propylene glycol coordination complex of aluminum chlorohydrate sold under this tradename by Reheis Chemical Company.

(e) Rezal 36 G is a 35% solution of a coordination complex of aluminum zirconium tetrachlorohydrate and glycine, sold under this tradename by Reheis Chemical Company.

(f) Zirconium oxychloride is $ZrOCl_2.8H_2O$ (g) Iron (III) nitrate is $Fe(NO_3)_3.9H_2O$ (h) Zinc acetate is $Zn(CH_3COO)_2.2H_2O$ (i) Zinc sulfate is $ZnSO_4.nH_2O$, where n=6 to 7.

(j) Cerium (IV) sulfate is $Ce(HSO_4)_4$ (k) Cerium (III) nitrate is $Ce(NO_3)_3.6H_2O$ (l) Iron (III) chloride is $FeCl_3.6H_2O$ (m) Iron (III) sulfate is $Fe_2(SO_4)_3.nH_2O$, where n=5 to 6.

(n) Sodium sulfate is $Na_2SO_4$ (o) Sodium chloride is NaCl (p) Calcium acetate is $Ca(CH_3COO)_2.H_2O$ (q) Magnesium sulfate is $MgSO_4.7H_2O$

EXAMPLE 1

Float/Sink Behavior Of Hair Treated With Compositions Containing Polyvalent Metal Salts As A Measure Of Hydrophobicity A series of aqueous solutions were prepared each containing a different concentration of polyvalent metal salt as disclosed below. For comparison, aqueous solutions of monovalent alkali metal salts were also prepared.

The hydrophobicity of tinted hair and of bleached/waved hair was measured before and after treating the hair with the aqueous solutions by the float/sink method. Individual hair samples were treated separately by one of the Rinse and Leave-on Methods. The variations and salts employed follow along with their float/sink behavior.

| Salt (%) in Distilled Water | Treatment Method(s)[a] | Float/Sink Behavior[b] | |
| --- | --- | --- | --- |
| | | Tinted Hair | Bleached/Waved Hair |
| Untreated control | None | Sink | Sink |
| Aluminum sulfate (1%) | A, B, C | Float | Float |
| Aluminum sulfate (5%) | A, B, C | Float | Float |
| Aluminum sulfate (0.01%) | A, B, C, D, E, F, G, H | — | Float |
| Aluminum sulfate (0.05%) | E, F, G, H | — | Float |
| Aluminum chloride (1%) | A, B | Float | Float |
| Aluminum chloride (5%) | A, B | Float | Float |
| Chlorhydrol (5%) | B | — | Float |
| Rehydrol II (5%) | B | — | Float |
| Rezal 36G (5%) | B | — | Float |
| Cerium (IV) sulfate (1% suspension) | A, B, C, D | — | Float |
| Cerium (III) nitrate (1%) | A, B | — | Float |
| Iron (III) chloride (1%) | A, B, C, D | — | Float |
| Iron (III) sulfate (1%) | A, B, C, D | — | Float |
| Iron (III) nitrate (1%) | A, B, C, D | — | Float |
| Zirconium oxychloride (5%) | A | — | Float |
| Zinc acetate (5%) | A | — | Sink Slowly |
| Zinc sulfate (5%) | B | — | Sink Slowly |
| Calcium acetate (1%) | A, B, C, D | — | Sink |
| Magnesium sulfate (5%) | B | — | Sink |
| Sodium sulfate (1%) | A, B, C, D | — | Sink |
| Sodium chloride (1%) | A, B, C, D | — | Sink |

[a]One tress per treatment; See Section V for procedure.
[b]Sink means the hair fibers sink within 30 seconds; sink slowly means the hair fibers sink between 30 seconds and 2 minutes; float means the hair fibers float more than one hour.

The results show, that in Rinse Methods A–D, hydrophobicity was restored to tinted and bleached/waved hair by hair treatments with the salt solutions containing polyvalent cations of aluminum, cerium, iron and zirconium and the solutions containing coordination complexes of aluminum and aluminum zirconium (Rehydrol II and Rezal 36G).

In studies with aluminum sulfate, the results show that lasting hydrophobicity was restored to bleached/waved hair at an operable salt concentration of as low as 0.01 weight percent from either the Rinse Methods A–D or the Leave-on Methods E–H.

On the other hand, hydrophobicity was not restored to bleached/waved hair by any of the Rinse treatments with solutions containing the polyvalent salts of calcium, magnesium and zinc or the monovalent sodium salts.

EXAMPLE 2

Hydrophobicity Of Aluminum Treated Hair Measured By Water-droplet Spreading

This example demonstrates the restoration of hydrophobicity to bleached/waved hair by treating it following Rinse Method B with an aluminum salt. One bleached/waved tress was treated with an aqueous solution of aluminum sulfate present at a concentration of 1 weight percent.

The hydrophobicity of the treated tress was observed following the water-droplet spreading procedure of II as compared against that of an untreated counterpart tress. The water droplet spread immediately over the untreated hair showing no hydrophobicity whereas the treated hair was hydrophobic. The water droplet did not spread over the surface of the aluminum treated hair within a period of an hour.

EXAMPLE 3

Hair Treating Composition Containing Conditioner

This example shows the ability of an aluminum salt to impart hydrophobicity to tinted and to bleached/waved hair even when the salt is incorporated into an oil-in-water emulsion comprised of cationic, nonionic and anionic emulsifiers and conditioners. The example further demonstrates that the hydrophobic effect imparted by the aluminum-containing composition is achieved even in the presence of relatively high concentrations of cationic-type conditioner materials present in the formula that normally soften the hair and leave it limp.

One tinted and one bleached/waved tress was treated with Conditioner A, containing no aluminum salt following the procedures of Rinse Method B. A similar set of tresses were treated with Conditioner A following Rinse Method D. A parallel test was made using similar sets of tinted and bleached/waved tresses following Methods B and D, except that Conditioner B was used containing 0.2 weight percent of aluminum sulfate.

The composition of Conditioners A and B and the results obtained from the Float/Sink test follow.

| Ingredients In Conditioner Compositions | % By Weight A | % By Weight B |
|---|---|---|
| PEG-2 Oleamonium chloride[a] (and) isopropyl alcohol | 2.5 | 2.5 |
| Quaternium-26[b] | 0.05 | 0.05 |
| Stearamidopropyl dimethylamine[c] | 0.2 | 0.2 |
| PEG-75[d] | 1.5 | 1.5 |
| Glyceryl stearate SE[e] | 1.5 | 1.5 |
| Stearic acid | 1.5 | 1.5 |
| Cetyl alcohol | 2.5 | 2.5 |
| Cyclomethicone[f] | 1.0 | 1.0 |
| Aluminum sulfate | — | 0.2 |
| Fragrance, Color, Preservation and others | 0.8 | 0.8 |
| Water to 100 grams | q.s. | q.s. |
| Phosphoric acid to pH about 3–3.5 | q.s. | q.s. |
| Float/Sink Behavior of Tinted Hair | | |
| Treated by Method B | Sink | Float |
| Treated by Method D | Sink | Float |
| Float/Sink Behavior of Bleached/Waved Hair | | |
| Treated by Method B | Sink | Float |
| Treated by Method D | Sink | Float |

[a]CTFA name for a Polyoxyethylene (2) oleamonium chloride. Sold under the trademark Ethoquad 0/12 by the Armak Company.
[b]CTFA name for Minkamidopropyl dimethyl 2-hydroxyethyl ammonium chloride. CAS Number: 68953-64-0
[c]CTFA name for dimethylaminopropyl stearamide
[d]CTFA name for a polymer of ethylene oxide having an average value of 75 moles ethylene oxide.
[e]SE means self-emulsifying grade that contains some sodium and/or potassium stearate.
[f]CTFA name for a cyclic dimethylpolysiloxane having an average of about 3 to 6 dimethylsiloxane units.

The results show that the aluminum containing Conditioner B imparts hydrophobicity to tinted and to bleached/waved hair whereas Conditioner A without the aluminum salt does not.

EXAMPLE 4

Improved Physical Properties Of Treated Bleached/waved Hair

Bleached/waved hair fibers normally tend to adhere or clump together when the hair is wet. On drying, therefore, the hair fiber mass tends to have a "bunched" appearance rather than a soft fluffy look. This example illustrates the improved physical property of bleached/waved hair, on drying, treated with polyvalent aluminum and iron salts compared against those of non-conditioning polyvalent alkali earth and monovalent alkali metal salts.

Each tress was treated with a different metal salt by following a Rinse method or a Leave-on method as shown below. The effect on the physical properties of the metal-salt treated bleached/waved hair was evaluated by the following method.

(1) The treated tress was thoroughly wetted with water. The excess water was stripped off the hair fibers by placing two fingers near the scalp portion of the tress and stripping the hair once with a downward motion to the ends portion of the tress. This stripping action aligned the fibers into a single adhering mass. The tress was hung on a rack and allowed to dry naturally under ambient room conditions. On drying, the appearance of the tress was visually examined to see if the fibers had separated giving the hair a fluffy soft look or if they had remained adhered giving the hair a stiff bunched look.

(2) After evaluating the treated tresses, they were washed in the usual manner with a conventional commercial non-soap, detergent shampoo. The procedure of step 1 was repeated and the physical properties of the tresses reexamined.

The various metal salts and treatment methods used and the results observed were as follows. Except for the emulsion Conditioners A and B, the treatments were aqueous solutions of the metal salt.

| Aqueous Composition | Treatment Method(s) | Physical Properties of Dry Bleached/Waved Hair After Treatment (Step 1) | After a Subsequent Shampoo (Step 2) |
|---|---|---|---|
| Untreated Control | None | Bunched | Bunched |
| Aluminum Sufate (1%) | A, B | Fluffy | Fluffy |
| Aluminum Sulfate (10%) | A, B | Fluffy | Fluffy |
| Aluminum Sulfate (0.05%) | E, F | Fluffy | Fluffy |
| Aluminum Sulfate (0.01%) | A, B, E, F | Fluffy | Fluffy |
| Aluminum Chloride (1%) | A, B | Fluffy | Fluffy |
| Aluminum Chloride (10%) | A, B | Fluffy | Fluffy |
| Iron (III) Nitrate (1%) | A, B | Fluffy | Fluffy |
| Iron (III) Sulfate (1%) | A, B | Fluffy | Fluffy |
| Calcium Acetate (1%) | A, B | Bunched | Bunched |
| Sodium Sulfate (1%) | A, B, E, F | Bunched | Bunched |
| Conditioner A of Example 3 | B | Sl. Bunched | Bunched |
| Conditioner B of Example 3 | B | Fluffy | Fluffy |

Bleached/waved tresses treated with aluminum or iron salts dried to a natural fluffy appearance whereas tresses similarly treated with calcium or sodium salt remained as bunched in appearance as were untreated bleached/waved control tresses. The results further show that the conditioning benefit if the aluminum and iron salt treatments persisted through a subsequent shampoo step.

EXAMPLE 5

Bodying Effects From Hair Treatments

This example illustrates the bodying effect of a hair treatment on bleached/wave hair using an aluminum salt. Two bleached/waved tresses were treated with an aqueous soultion of aluminum sulfate present at a concentration of 1 weight percent following method B. For comparison, two bleached/waved tresses were similarly treated, except that water was used instead of the salt solution.

The tresses were combed and rated for body, i.e., thickness, fullness and fluffiness, on a scale of 1 to 5 by 5 experienced evaluators. The results were as follows:

| Tress | Treatment | Body[a] (Average rating of 5 evaluators) |
|---|---|---|
| 1 | Aluminum Sulfate (1%) | 4.4 |
| 2 | Aluminum Sulfate (1%) | 3.8 |
| 3 | Water | 1.8 |
| 4 | Water | 1.6 |

[a]Body Rating: 5 = Excellent; 4 = Good; 3 = Fair; 2 = Poor; 1 = Very Poor.

The results show that the metal salt treated bleached/waved hair was bodied whereas the water-treated control was not bodied.

EXAMPLE 6

Effect Of Hair Treatment On Set Retention Properties Of Hair

This example illustrates the improved set retention of hair from a hair treatment with an aluminum salt compared to that of untreated hair.

For this test, natural brown tresses of normal human hair (DeMeo Brothers, New York) 15.24 cm (about 6 inches) in length and 2 grams in weight were used. One series of tresses was used intact and one series of tresses was waved with a commercial permanent wave product containing ammonium thioglycolate (about 10% as thioglycolic acid and pH about 9) following the product's package instructions.

A series of 5 normal hair tresses and 5 waved tresses was treated with an aqueous solution of aluminum chloride present at a concentration of 5 weight percent following Rinse Method B. A second similar series of tresses was treated with water.

Set retention was measured as follows. Each tress was dampened with about 2 ml. of water, combed through once and wound on conventional hair setting rollers of about 1.59 cm (⅝ inch) in diameter. The set tresses were dried under ambient room conditions overnight. The rollers were removed and the tress was styled into a single curl. The hanging length of the curl was measured and recorded at time zero. The curled tresses were subsequently allowed to relax under their own hanging weight at ambient conditions of 50 to 60% relative humidity (RH).

The hanging length of the normal hair series was measured after 24 hours and the hanging length of the waved hair series was measured after 10 days and the % set retained calculated from the following formula:

$$\frac{L - L_t}{L - L_o} \times 100$$

where L = tress straight length = 15.24 cm; $L_o$ = tress hanging length at time zero; and $L_t$ = tress hanging at time t.

The results were as follows

| Hair | Treatment | Tress Hanging Length (cm) | | | % Set Retained[a] |
| --- | --- | --- | --- | --- | --- |
| | | 0 Hr. | 24 Hrs. | 10 Days | |
| Normal | 5% aluminum chloride | 1.6 | 6.3 | | 66 |
| Normal | water | 1.5 | 7.5 | | 56 |
| Waved | 5% aluminum chloride | 0.7 | | 2.1 | 90 |
| Waved | water | 1.0 | | 4.1 | 78 |

[a] average of five tresses for each treatment.

The results showed that the aluminum salt-treated normal and waved hair tresses had better set retention at 50–60% RH than did their respective water-treated counterparts.

EXAMPLE 7

Effect Of Hair Treatment On The Porosity Of Bleached/Waved Hair

The Method B procedure of Example 3 was followed, except that the porosity of bleached/waved hair was measured relative to its water absorption using a method for determining liquid retention values similar to that described by Wolfram and Underwood in *Textile Research Journal* 36(11), pp. 947–953 (1966) incorporated herein by reference, except that water was used instead of a buffer solution for soaking the hair. The more porous the hair is, the greater the liquid retention value becomes. The data were as follows:

| Treatment | % Liquid Retained (average of 4 determinations) |
| --- | --- |
| Conditioner A, Example 3 | 58.6 |
| Conditioner B, Example 3 | 55.3 |
| Untreated Control | 59.6 |

A statistical analyses of the results by the well known Student's t test showed that:

(a) Hair treated with a conventional conditioner (Composition A) was not significantly different in liquid retention value from the untreated hair control.

(b) Hair treated with Composition B (containing 0.2% aluminum sulfate) was significantly lower in liquid retention value than both the untreated control and the hair treated with Composition A only, both at 99% confidence levels.

Thus, in the hair treatment practiced herein, the porosity of bleached/waved hair was significantly reduced with a hair treating composition containing a small amount (0.2%) of polyvalent metal salt.

EXAMPLE 8

On-head Evaluation Of Hair Treatments

This example illustrates the effect of aluminum salt treatment evaluated with volunteer females under salon conditions. In each study, half of the panelists had normal hair and the remaining half had tinted hair.

For these studies, a conventional commercial conditioner was used for experiment #1 and a different conventional commercial conditioner was used for experiment #2. In half-head comparison tests, the commercial conditioner was used on one side following treatment Method B. On the opposite side of the head, the hair was treated with the same commercial conditioner containing added 0.2 weight percent aluminum sulfate.

In experiment #1, 6 subjects were used. Evaluation results of the half-heads by experienced beauticians showed that the hair on the side treated with the aluminum salt-containing conditioner was better in overall appearance, had better condition on the ends, better sheen and was less coated than the side treated without aluminum.

In experiment #2, 12 subjects were used. In this experiment the subjects had their hair styled by setting it on rollers and drying it in the usual manner or by blow drying it with a hair dryer, whichever option was preferred by the volunteer. The beauticians commented that the hair on the side treated with the aluminum-containing composition was easier to work with during setting and styling. The hair on the metal salt-treated side had more body on drying than did the hair on the side treated without the polyvalent metal salt.

The present invention has been described with respect to preferred embodiments. It will be clear to those skilled in the art that modifications and/or variations of the disclosed compositions and methods can be made without departing from the scope of the invention set forth herein. The invention is defined by the claims that follow.

What is claimed is:

1. A method of treating hair for purposes of strengthening and improving the physical properties thereof comprising the steps of contacting the hair with an aqueous hair treating composition having a pH value of about 2 to about 7 and including about 0.001 to about 10 weight percent of a water-dispersible, non-toxic polyvalent metal salt of a mineral acid selected from the group consisting of aluminum sulfate, aluminum chloride, cerium (III) nitrate, ferric chloride, ferric sulfate, ferric nitrate, aluminum chlorohydrate, a propylene glycol coordination complex of aluminum chlorohydrate, a coordination complex of aluminum zirconium tetrachlorohydrate and glycine and mixtures thereof, rubbing the composition into the hair and maintaining said composition thereon for a period of at least 6 to about 24 hours.

2. The method of claim 1 wherein said metal salt of a mineral acid is aluminum sulfate.

* * * * *